US009050018B2

(12) United States Patent
Rapoport

(10) Patent No.: US 9,050,018 B2
(45) Date of Patent: Jun. 9, 2015

(54) MEANS AND METHODS FOR PROVIDING HIGH RESOLUTION MRI

(75) Inventor: Uri Rapoport, Moshav Ben Shemen (IL)

(73) Assignee: ASPECT IMAGING LTD, Shoham (IL)

( * ) Notice: Subject to any disclaimer, the term of this patent is extended or adjusted under 35 U.S.C. 154(b) by 739 days.

(21) Appl. No.: 13/143,937

(22) PCT Filed: Jan. 13, 2010

(86) PCT No.: PCT/IL2010/000031
§ 371 (c)(1),
(2), (4) Date: Aug. 30, 2011

(87) PCT Pub. No.: WO2010/082193
PCT Pub. Date: Jul. 22, 2010

(65) Prior Publication Data
US 2011/0304333 A1 Dec. 15, 2011

(30) Foreign Application Priority Data
Jan. 13, 2009 (IL) .......................................... 196487

(51) Int. Cl.
*G01V 3/00* (2006.01)
*A61B 5/055* (2006.01)
*G01R 33/38* (2006.01)
*G01R 33/381* (2006.01)
*G01R 33/561* (2006.01)
*G01R 33/565* (2006.01)
*G01R 33/567* (2006.01)

(52) U.S. Cl.
CPC ................ *A61B 5/055* (2013.01); *G01R 33/38* (2013.01); *G01R 33/3806* (2013.01); *G01R 33/381* (2013.01); *G01R 33/5617* (2013.01); *G01R 33/56554* (2013.01); *G01R 33/56563* (2013.01); *G01R 33/56581* (2013.01); *G01R 33/5676* (2013.01)

(58) Field of Classification Search
CPC ..................................................... G01R 33/38
USPC .......................... 324/309, 307, 306, 312, 314
See application file for complete search history.

(56) References Cited

U.S. PATENT DOCUMENTS

| | | | | |
|---|---|---|---|---|
| 5,910,112 | A | * 6/1999 | Judd et al. ...................... | 600/410 |
| 6,043,656 | A | * 3/2000 | Ma et al. ........................ | 324/309 |
| 7,215,119 | B2 | * 5/2007 | Kruger et al. ................. | 324/312 |
| 8,851,018 | B2 | 10/2014 | Rapoport et al. | |
| 2003/0181821 | A1 | 9/2003 | Greenwald et al. | |
| 2007/0249928 | A1 | 10/2007 | Blezek et al. | |
| 2007/0265520 | A1 | 11/2007 | Posse | |
| 2011/0162652 | A1 | 7/2011 | Rapoport | |
| 2011/0186049 | A1 | 8/2011 | Rapoport | |
| 2011/0234347 | A1 | 9/2011 | Rapoport | |
| 2011/0304333 | A1 | 12/2011 | Rapoport | |
| 2012/0071745 | A1 | 3/2012 | Rapoport | |
| 2012/0073511 | A1 | 3/2012 | Rapoport et al. | |
| 2012/0077707 | A1 | 3/2012 | Rapoport | |
| 2012/0119742 | A1 | 5/2012 | Rapoport | |
| 2013/0079624 | A1 | 3/2013 | Rapoport | |
| 2013/0109956 | A1 | 5/2013 | Rapoport | |
| 2013/0237803 | A1 | 9/2013 | Rapoport | |
| 2013/0328559 | A1 | 12/2013 | Rapoport | |
| 2013/0328560 | A1 | 12/2013 | Rapoport | |
| 2013/0328563 | A1 | 12/2013 | Rapoport | |
| 2014/0050827 | A1 | 2/2014 | Rapoport | |
| 2014/0051973 | A1 | 2/2014 | Rapoport et al. | |
| 2014/0051974 | A1 | 2/2014 | Rapoport et al. | |
| 2014/0051976 | A1 | 2/2014 | Rapoport et al. | |
| 2014/0099010 | A1 | 4/2014 | Rapoport et al. | |
| 2014/0103927 | A1 | 4/2014 | Rapoport | |
| 2014/0117989 | A1 | 5/2014 | Rapoport | |
| 2014/0128725 | A1 | 5/2014 | Rapoport et al. | |
| 2014/0139216 | A1 | 5/2014 | Rapoport | |
| 2014/0142914 | A1 | 5/2014 | Rapoport | |
| 2014/0152302 | A1 | 6/2014 | Rapoport et al. | |
| 2014/0152310 | A1 | 6/2014 | Rapoport | |
| 2014/0158062 | A1 | 6/2014 | Rapoport et al. | |
| 2014/0230850 | A1 | 8/2014 | Rapoport | |
| 2014/0257081 | A1 | 9/2014 | Rapoport | |
| 2014/0266203 | A1 | 9/2014 | Rapoport et al. | |
| 2014/0300358 | A1 | 10/2014 | Rapoport | |
| 2014/0378821 | A1 | 12/2014 | Rapoport et al. | |
| 2014/0378825 | A1 | 12/2014 | Rapoport et al. | |

(Continued)

OTHER PUBLICATIONS

Aspect Imaging Ltd, "MRI-Incubator's Closure Assembly", co-pending U.S. Appl. No. 14/539,442, filed Nov. 12, 2014.
Aspect Imaging Ltd., "Shutting Assembly for Closing an Entrance of an MRI Device", co-pending U.S. Appl. No. 14/540,163, filed Nov. 13, 2014.
Aspect Imaging Ltd., "Cage in an MRD with a Fastening/Attenuating System", co-pending U.S. Appl. No. 14/527,950, filed Oct. 30, 2014.
Rapoport, URI, "RF Shielding Conduit in an MRI Closure Assembly", co-pending U.S. Appl. No. 14/574,785 filed Dec. 18, 2014.
Aspect Imaging Ltd., "System and Method for Generating Invasively Hyperpolarized Images", co-pending U.S. Appl. No. 14/556,682 filed Dec. 1, 2014.

(Continued)

*Primary Examiner* — Louis Arana
(74) *Attorney, Agent, or Firm* — The Law Office of Michael E. Kondoudis

(57) ABSTRACT

Means and methods for improving the MRI "image quality in an MRI imaging" apparatus comprising a non-superconducting electromagnet and a plurality of pole pieces are provided. Said means for improving the image quality chosen from the group consisting of (a) means for reducing degradation of MRI image quality due to $B_0$ field instability; (b) means for decreasing or otherwise correcting residual magnetization; (c) means for providing a 3D scout image; and (d) any combination of the above. These means for improving the image quality provides greater resolution of the imaged object relative to an MRI apparatus not containing such means for improving image quality.

6 Claims, No Drawings

(56) References Cited

U.S. PATENT DOCUMENTS

2015/0059655 A1    3/2015   Rapoport
2015/0065788 A1    3/2015   Rapoport

OTHER PUBLICATIONS

Aspect Imaging Ltd., "System and Method for Generating Invasively Hyperpolarized Images", co-pending U.S. Appl. No. 14/556,654 filed Dec. 1, 2014.
Aspect Imaging Ltd., "Means for Operating an MRI Device Within a RF-Magnetic Environment", co-pending U.S. Appl. No. 14/596,320 filed Jan. 14, 2015.
Aspect Imaging Ltd., "Means and Method for Operating an MRI Device Within a RF-Magnetic Environment", co-pending U.S. Appl. No. 14/596,329 filed Jan. 14, 2015.
Aspect Imaging Ltd., "CT/MRI Integrated System for the Diagnosis of Acute Strokes and Methods Thereof", co-pending U.S. Appl. No. 14/598,517 filed Jan. 16, 2015.
Aspect Imaging Ltd., "RF Automated Tuning System Used in a Magnetic Resonance Device and Methods Thereof", co-pending U.S. Appl. No. 14/588,741 filed Jan. 2, 2015.
Aspect Imaging Ltd., "MRI With Magnet Assembly Adapted for Convenient Scanning of Laboratory Animals With Automated RF Tuning Unit", co-pending U.S. Appl. No. 14/581,266 filed Dec. 23, 2014.
Aspect Imaging Ltd., "Foamed Patient Transport Incubator", co-pending U.S. Appl. No. 14/531,289, filed Nov. 3, 2014.
Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Aspect Imaging Ltd., "Method for Providing High Resolution, High Contrast Fused MRI Images", co-pending U.S. Appl. No. 13/877,553, filed Apr. 3, 2013.
Aspect Imaging Ltd., "Method for Manipulating the MRI's Protocol of Pulse-Sequences", co-pending U.S. Appl. No. 14/070,695, filed Nov. 4, 2013.

* cited by examiner

MEANS AND METHODS FOR PROVIDING HIGH RESOLUTION MRI

FIELD OF THE INVENTION

The present invention generally relates to MRI. More specifically, the invention concerns means and methods for providing high resolution MRI.

BACKGROUND OF THE INVENTION

ASPECT Magnet Technologies Ltd (Israel) markets commercially available NMR/MRI devices. Those medical-grade (1-1.5 Tesla), desktop-size, high-resolution Magnetic Resonance Imaging (MRI) based system for laboratories and pre-clinical research centers performing in-vivo small animal imaging and in-vitro studies. In addition, a MRI system is also being developed for human extremities applications, with Carpal Tunnel Syndrome (wrist) as the first medical application.

As concerns to $B_0$ Field Stability, a large drift in frequency during scan, specifically when very high resolution images are required. "Very high resolution" is dependent on the S/N available per acquired data and scan time, e.g. 100 um×100 um×500 um is considered as high resolution on the Aspect MRI scanner.

Instability occurs as a result of: a. Environment change in temperature; b. Gradient Ohmic heating; and c. External fields. Means and methods for reducing the sensitivity of an imaging system, as described, to $B_0$ field instability are still a long felt need.

As concerns to On Fast SE, FSE is sensitive to gradient performance as well as $B_0$ stability.

Artifacts such as interference patterns and/or ghosts will appear on the magnitude image.

After eliminating the problem of eddy currents the following still remain to be solved:
a. Inaccurate gradient response to the designed pulses.
b. Residual magnetization in magnets with magnetic permeable pole pieces.
c. Concomitant magnetic fields ("Maxwell fields") due to high gradient fields with respect to the $B_0$ field of the magnet. These will cause an unwanted spatial distribution of magnetic field which will cause spin phase evolution in accordance.

As concerns to 3D scout, there is a long felt need relates to how to achieve the shortest procedure in order to localize a scan to visualize an object.

SUMMARY OF THE INVENTION

It is a object of the invention herein disclosed to disclose, in an MRI apparatus comprising a non-superconducting electromagnet and a plurality of pole pieces, means for reducing degradation of MRI image quality due to $B_0$ field instability by decreasing sensitivity to said $B_0$ field instability, said, means comprising (a) means for correcting for drift of the excitation volume, said correcting means comprising means for applying broad band RF excitation pulses with strong selection gradients and/or means for providing a real time change in the TX frequency adapted to obtain a smooth change during the scan; and (b) means for correcting for drift of the frequency and/or phase of the acquired data, said means comprising means for obtaining a linear phase correction (F) of each FID of the functional form $F=\Delta f(t+t_e)$. It is in the essence of the invention wherein said means for i reducing degradation of MRI image quality due to $B_0$ field instability by decreasing sensitivity to said $B_0$ field instability enables reduction in at least one of the following relative to an MRI apparatus identical to said MRI apparatus other than lacking said means for increasing or providing $B_0$ field stability without reduction in the imaging resolution: (a) distance between item being imaged and at least one of said electromagnets; (b) magnetic field; (c) temperature of said electromagnet.

It is a further object of this invention to disclose, in an MRI apparatus comprising a non-superconducting electromagnet and a plurality of pole pieces, means for decreasing or otherwise correcting residual magnetization, said means comprising (a) means for providing extra gradient pulses adapted to restore the magnetization of said plurality of pole pieces; and (b) means for providing at least one high current pulse to said electromagnet. It is in the essence of the invention wherein said means for decreasing or otherwise correcting residual magnetization enables accumulation 2D or 3D MRI images with higher resolution relative to an MRI apparatus identical to said MRI apparatus other than lacking said means for decreasing or otherwise correcting residual magnetization.

It is a further object of this invention to disclose, in an MRI apparatus comprising a non-superconducting electromagnet and a plurality of pole pieces, means for providing a 3D scout image, said means comprising (a) means for providing a 3D short TR scan in the volume of interest; (b) means for reconstructing three orthogonal main axis slices; and (c) means for transmitting said axis slices to 3-plane localizer software. It is within the essence of the invention wherein said means for providing a 3D scout image enable said apparatus to localize the imaged object and to restrict the volume in which an MRI image is obtained to the minimum necessary to image said object.

It is a further object of this invention to disclose, in an MRI apparatus comprising a non-superconducting electromagnet and a plurality of pole pieces, means for providing Fast Spin-Echo (FSE) MRI, said means comprising: (a) means for FSE calibration, said means comprising means for separating the odd and even echoes; (b) means for calculating the shift in time and phase of said odd and even echoes; (c) means for correcting residual magnetization, said means comprising: (i) means for providing extra gradient pulses adapted to restore the magnetization of said plurality of pole pieces; and (ii) means for providing at least one high current pulse to said electromagnet; and (d) means for correcting concomitant fields. It is within the essence of the invention wherein said means for providing FSE MRI increases the resolution of acquired images, and minimizes the time necessary for acquisition of said images, relative to an MRI apparatus identical to said apparatus other than lacking said means for providing FSE MRI.

It is a further object of this invention to disclose, in an MRI apparatus comprising a non-superconducting electromagnet and a plurality of pole pieces, means for providing Fast Spin-Echo (FSE) MRI, said means comprising (a) means for FSE calibration, said means comprising means for separating the odd and even echoes; (b) means for calculating the shift in time and phase of said odd and even echoes; (c) means for correcting residual magnetization, said means comprising (i) means for providing extra gradient pulses adapted to restore the magnetization of said plurality of pole pieces; and (ii) means for providing at least one high current pulse to said electromagnet; (d) means for correcting concomitant fields; and (e) means for providing a 3D scout image, said means comprising: (i) means for providing a 3D short TR scan in the volume of interest; (ii) means for reconstructing three orthogonal main axis slices; and (iii) means for transmitting said axis slices to 3-plane localizer software. It is within the essence of the invention wherein said means for providing FSE MRI increases the resolution of acquired images, and minimizes the time necessary for acquisition of said images, relative to an MRI apparatus identical to said apparatus other than lacking said means for providing FSE MRI.

It is a further object of this invention to disclose, in an MRI apparatus comprising a non-superconducting electromagnet and a plurality of pole pieces, a method for reducing degradation of MRI image quality due to $B_0$ field instability by decreasing sensitivity to said $B_0$ field instability, said method comprising steps of (a) correcting drift of the excited volume; and (b) correcting drift of the observed frequency and phase of the acquired data.

It is a further object of this invention to disclose such a method, wherein said step of correcting drift of the excited volume further comprises a step of applying broadband RF excitation pulses with strong selection gradients.

It is a further object of this invention to disclose such a method, wherein said step of correcting drift of the excited volume further comprises as step of changing the TX frequency in real time.

It is a further object of this invention to disclose such a method, wherein said step of correcting drift of the observed frequency and phase of the acquired data further comprises a step of collecting extra navigator echoes during the scan.

It is a further object of this invention to disclose, in an MRI apparatus comprising a non-superconducting electromagnet and a plurality of pole pieces, a method for decreasing or otherwise correcting residual magnetization, comprising steps of (a) providing extra gradient pulses adapted to restore the magnetization of said plurality of pole pieces; and (b) optionally, providing a high current pulse adapted to restore the magnetization of said plurality of pole pieces.

It is a further object of this invention to disclose, in an MRI apparatus comprising a non-superconducting electromagnet and a plurality of pole pieces, a method for providing a 3D scout image, said method comprising steps of (a) performing a 3D short TR scan; (b) reconstructing three orthogonal main magnetic axis slices; and (c) using said magnetic axis slices in 3-plane localizer software.

It is a further object of this invention to disclose, in an MRI apparatus comprising a non-superconducting electromagnet and a plurality of pole pieces, a method for increasing or otherwise providing Fast Spin-Echo (FSE) MRI, said method comprising steps of (a) calibrating said FSE, said calibrating comprising steps of (i) separating odd and even echoes; and (ii) calculating the shift in time and phase of said odd and even echoes; (b) correcting for residual magnetization; and (c) correcting for concomitant fields.

It is a further object of this invention to disclose such a method, wherein said step of correcting for concomitant fields further includes the additional steps of (a) separating odd and even echoes; and (b) applying a reconstruction algorithm, said reconstruction algorithm comprising steps of (i) reconstructing separately images of said odd and even echoes; (ii) deriving a low resolution phase correction from data sets of said odd and even echoes; (iii) performing a low resolution phase correction according to the protocol derived in step (ii); and (iv) combining said images of said odd and even echoes.

It is a further object of this invention to disclose such a method, wherein said step of separating odd and even echoes further comprises the additional step of applying a crusher gradient for every other echo along the train.

It is a further object of this invention to disclose such a method, wherein said step of separating odd and even echoes further comprises steps of: (a) applying a phase cycling scheme consisting of 0° and 180° pulses in modulator phase for every other 180° refocusing pulse to one of a two-excitation scan; and (b) adding and subtracting said two scans until the desired separation is achieved.

It is a further object of this invention to disclose such a method, further comprising a step of obtaining a 3D scout image.

It is a further object of this invention to disclose such a method, wherein said step of obtaining a 3D scout image comprises further steps of (a) performing a 3D short TR scan; (b) reconstructing three orthogonal main magnetic axis slices; and (c) using said magnetic axis slices in 3-plane localizer software.

It is a further object of this invention to disclose the means and methods as defined in any of the above, wherein said MRI apparatus is an MRI apparatus commercially available from ASPECT.

In a commercially MRI and especially an ASPECT MRI, the present invention discloses means for decreasing sensitivity to $B_0$ field instability, thus eliminating degradation of image quality due to $B_0$ field instability, as defined in the present invention.

In a commercially MRI and especially an ASPECT MRI, the present invention further discloses a method for decreasing sensitivity to $B_0$ field instability, thus eliminating degradation of image quality due to $B_0$ field instability, comprising steps as defined in the present invention.

In a commercially MRI and especially an ASPECT MRI, In an MRI, the present invention further discloses means for increasing or otherwise providing Fast SE as defined in the present invention.

In a commercially MRI and especially an ASPECT MRI, In an MRI, the present invention further discloses a method for increasing or otherwise providing Fast SE, comprising steps as defined in the present invention.

In a commercially MRI and especially an ASPECT MRI, the present invention further discloses means for decreasing or otherwise correcting Residual magnetization as defined in the present invention.

In a commercially MRI and especially an ASPECT MRI, the present invention further discloses method for decreasing or otherwise correcting Residual magnetization, comprising steps as defined in the present invention.

In a commercially MRI and especially an ASPECT MRI, the present invention further discloses means for providing 3D scout as defined in the present invention.

In a commercially MRI and especially an ASPECT MRI, the present invention further discloses method for providing 3D scout, comprising steps as defined in the present invention.

DETAILED DESCRIPTION OF THE PREFERRED EMBODIMENTS

The following description is provided so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide means and methods for providing high resolution MRI.

As used herein, the term "high current pulse" refers to a pulse in which the current is higher than any other current in the pulse sequence in the gradient.

$B_0$ Field Stability

The present invention provides novel means for decreasing sensitivity to $B_0$ field instability, thus eliminating degradation of image quality due to instabilities in the $B_0$ field.

There are two subjects in this matter that need to be attended to:
  a. Drift of the excited volume (with excitation number);
    i. In 2D scans the drift can be considerably reduced by applying broad band RF excitation pulses with strong selection gradients. In 3D scans the same can be done, however due to larger excited volumes the select gradient is weaker. If the encodings along the 3D will take the shortest possible time (e.g. the most inner loop of the scan) the problem is completely mitigated for the central reconstructed slices.
    ii. A real time change in TX frequency. The difficulty is to achieve a smooth change during the scan which requires accurate frequency measurements or a cumbersome algorithm. In any of the above in order to have good results (high resolution) we have to collect the frequencies for post processing as will be described next. A good compromise is to predict the behavior during scan and follow a predetermined set of TX frequencies.
  b. Drift of the acquired data in the observe frequency and phase (inconsistency of the acquired data)

Extra navigator echoes are collected during the scan and serve two purposes: (1) Change TX frequency during the scan as described above; (2) Post process the data during reconstruction of the images.

The navigator echoes are collected as an extra spin echo in FSE type scan and as an extra FID in SE and GRE types. The extra collected data is smoothed out and interpolated by a polyfit algorithm and used in the recon. algorithm.

GRE type scans suffer from data inconsistency (due to frequency drift) both in spatial shift and echo phase.

Correcting this inconsistency is done by a linear phase correction of each FID where the constant is the derived frequency drift and the constant is te*derived frequency drift. SE types are corrected in the same way with the constant set to zero.

On Fast SE

The present invention discloses mean and methods to provide Fast SE. In general, different spin phase evolution between different refocusing RF pulses is uncorrectable. A situation in which the evolution between refocusing pulses is repeating itself throughout the echo train, may be corrected for. In the following, the latter is assumed.

To create this condition some calibrations and modifications to the pulse sequence are necessary.
  a. FSE calibration:
  Under the said assumption/approximation a shift in gradient echo time and phase occurs along the echo train where the odd and the even echoes following an RF refocusing pulse are oppositely shifted (echo time and phase). This causes the wave (interference) and ghosting artifacts. The calibration procedure consists of the following:
    i. There are two ways to separate the odd and even echoes:
      1. Crusher gradient for every other echo along the train will crush either the odd or the even echoes.
      2. A phase cycling scheme consisting of 0 180 degrees in modulator phase for every other RF refocusing pulse is applied to one of a two-excitation scan. By adding and subtracting the two scans the wanted separation is achieved.
    Alternatively the phase cycling may be applied for the RF excitation pulse.
      Note: to apply the separation of echoes during the calibration phase the scan should be run with the encode gradients off.
    ii. To calculate the shift in time and phase of the odd/even echoes, a first FT is applied, the linear terms of the phase difference between the odd and even echoes is the resulting corrections needed in the pulse sequence. (constant→echo shift, constant→phase correction). These translate into a read dephase gradient correction and a phase hop in the TX which may be done by a frequency hop for a chosen duration.
  b. Residual magnetization:
  Since the encode gradient is changing throughout the echo train, depending on the pole piece behavior, the spin evolution along the train will not repeat itself. To correct for that, extra gradient pulses which restore the same magnetization in the pole piece are needed following each phase encode gradient pulse. If the conditions are sufficiently favorable, a single high current pulse will, to a good approximation, restore the same magnetization independent of gradient pulse history.
  c. Concomitant fields:
  The straight forward way to correct for concomitant fields is to compensate for the effect by applying gradients which have an opposite effect. This is very costly in the time scheme of a sequence and hence in SNR and scan time.

A better and robust way to correct the FSE scan is to apply a full scan odd/even echo separation as described above.

The reconstruction algorithm consists of separately reconstructing the images of the odd/even echoes, then combining them after performing a low resolution phase correction which is derived from the odd/even image data sets.

Residual Magnetization

As described in FSE corrections, paragraph b. This correction may be applied to all types of sequences when necessary. It also may be applied at the end or prior to an excitation cycle in order to achieve repeated initial conditions.

3D scout

The present invention discloses means and methods to provide 3D scout. In high resolution applications the scout scan needs to be a fairly high resolution in itself. In order to have a proper SNR as well, a 3D short TR scan is performed for the volume of interest.

Three orthogonal main magnetic axes slices are reconstructed to be used in a 3-plane localizer software. The targeted slices planes are reconstructed from the 3D data set and viewed. This considerably helps in locating the scan accurately in one go.

I claim:

1. In an MRI apparatus comprising a non-superconducting electromagnet and a plurality of pole pieces, means for improving the image quality, said means for improving the image quality comprising means for decreasing sensitivity to $B_0$ field instability; wherein said means for decreasing sensitivity to $B_0$ field instability comprises:
  a. means for correcting for drift of the excited volume comprising means for applying broad band RF excitation pulses with strong selection gradients and/or means for providing a real time change in the TX frequency adapted to obtain a smooth change during the scan; and
  b. means for correcting for drift of the frequency and/or phase of the acquired data, comprising means for collecting navigator echoes as extra FID and means for obtaining a linear phase correction function of each FID from said collected navigator echoes;
wherein said means for improving the image quality enables reduction in at least one of the following without reduction in the imaging resolution: (a) distance between item being imaged and at least one of said electromagnets; (b) magnetic field; (c) temperature of said electromagnet.

2. The means for improving image quality of claim 1, further comprising means for decreasing or otherwise correcting residual magnetization, wherein said means for decreasing or otherwise correcting residual magnetization comprises:
   a. means for providing extra gradient pulses adapted to restore the magnetization of said plurality of pole pieces; and,
   b. means for providing at least one high current pulse to said electromagnet;

wherein said means for decreasing or otherwise correcting residual magnetization enables accumulation 2D or 3D MRI images with higher resolution relative to an MRI apparatus identical to said MRI apparatus other than lacking said means for decreasing or otherwise correcting residual magnetization.

3. The means for improving image quality of claim 1, further comprising means for providing a 3D scout image, wherein said means for providing a 3D scout image comprises:
   a. means for providing a 3D short TR scan in the volume of interest;
   b. means for reconstructing three orthogonal main axis slices; and,
   c. means for transmitting said axis slices to 3-plane localizer software;

wherein said means for providing a 3D scout image enable said apparatus to localize the imaged object and to restrict the volume in which an MRI image is obtained to the minimum necessary to image said object.

4. In an MRI apparatus comprising a non-superconducting electromagnet and a plurality of pole pieces, a method for improving the image quality comprising a step of decreasing sensitivity to said $B_0$ field instability, said step of decreasing sensitivity to said $B_0$ field instability comprises:
   a. correcting drift of the excited volume, said correcting performed by applying RF excitation pulses with strong selection gradients, and/or changing TX frequency in real time; and,
   b. correcting drift of the observed frequency and/or phase of the acquired data by collecting extra navigator echoes during the scan, and calculating a linear phase correction function for each FID from said collected extra navigator echoes.

5. The method of claim 4 further comprising a step of decreasing or otherwise correcting residual magnetization, said step of decreasing or otherwise correcting residual magnetization comprises:
   a. providing extra gradient pulses adapted to restore the magnetization of said plurality of pole pieces; and,
   b. optionally, providing a high current pulse adapted to restore the magnetization of said plurality of pole pieces.

6. The method of claim 4 further comprising a step of providing a 3D scout image, said step of providing a 3D scout image comprises:
   a. performing a 3D short TR scan;
   b. reconstructing three orthogonal main magnetic axis slices; and,
   c. using said magnetic axis slices in 3-plane localizer software.

* * * * *